(12) United States Patent
Radosz et al.

(10) Patent No.: US 8,945,629 B2
(45) Date of Patent: Feb. 3, 2015

(54) NANOPARTICLES FOR CYTOPLASMIC DRUG DELIVERY TO CANCER CELLS

(75) Inventors: Maciej Radosz, Laramie, WY (US); Peisheng Xu, West Lafayette, IN (US); Youqing Shen, Laramie, WY (US)

(73) Assignee: University of Wyoming, Laramie, WY (US)

(*) Notice: Subject to any disclaimer, the term of this patent is extended or adjusted under 35 U.S.C. 154(b) by 2185 days.

(21) Appl. No.: 11/662,514

(22) PCT Filed: Sep. 8, 2005

(86) PCT No.: PCT/US2005/031887
§ 371 (c)(1),
(2), (4) Date: Mar. 6, 2009

(87) PCT Pub. No.: WO2007/001356
PCT Pub. Date: Jan. 4, 2007

(65) Prior Publication Data
US 2010/0203149 A1  Aug. 12, 2010

Related U.S. Application Data

(60) Provisional application No. 60/608,599, filed on Sep. 10, 2004, provisional application No. 60/643,623, filed on Jan. 13, 2005.

(51) Int. Cl.
*A61K 9/51* (2006.01)
*A61K 9/52* (2006.01)
*A61K 9/58* (2006.01)
*A61K 9/14* (2006.01)
*A61K 9/107* (2006.01)
*A61K 9/50* (2006.01)

(52) U.S. Cl.
CPC .............. *A61K 9/5146* (2013.01); *A61K 9/51* (2013.01); *A61K 9/1075* (2013.01); *A61K 9/5138* (2013.01); *A61K 9/5021* (2013.01); *A61K 9/5073* (2013.01)
USPC .......................... 424/497; 424/490; 424/649

(58) Field of Classification Search
None
See application file for complete search history.

(56) References Cited

U.S. PATENT DOCUMENTS

2002/0187199 A1* 12/2002 Ranger et al. ................ 424/501

OTHER PUBLICATIONS

Lee, R. J., et al. J. Biol. Chem. (1996), 271(14); p. 8481-8487.*
Endosome website (http://www.cytochemistry.net/cell-biology/medical/receptor_mediated_endocytosis_2.htm; available at least by Dec. 22, 2003, accessed online May 3, 2011).*
Leroux, J.-C. et al. J. Control. Release (2001), 72; p. 71-84.*

(Continued)

*Primary Examiner* — Kevin S Orwig
(74) *Attorney, Agent, or Firm* — Davis, Brown, Koehn, Shors & Roberts, P.C.; Kent A. Herink

(57) ABSTRACT

The invention is a nanoparticle that contains an anticancer drug that is released in cancer cells when administered to a subject. The nanoparticles have a core including the anticancer drug and polymer chains that are soluble at the pH of the cancer cell. The core is surrounded by a layer of polymer chains that are insoluble at the pH of healthy tissue but soluble at the pH of the cancer interstitium. An outside layer is made of water-soluble polymer chains to shield the nanoparticle from RES recognition and give the nanoparticle a long circulation time in the bloodstream of the subject. The outside layer may also include folic acid moieties that bind folic acid receptors on the surface of the cancer cell.

7 Claims, 4 Drawing Sheets

(56) References Cited

OTHER PUBLICATIONS

Fukushima, S., et al. JACS, 127; pp. 2810-2811; Pub. on Web Feb. 11, 2005.*
Kakizawa, Y., et al. Biomacromol. (2001), 2; pp. 491-497.*
Yoo, H. S., et al. J. Controlled Rel. (2004), 16; pp. 273-283.*
Kwon, G. S., et al. Adv. Drug Del. Rev. (1995), 16; pp. 295-309.*
Xu, et al.; "Anticancer Efficacies of Cisplatin-Releasing pH-Responsive Nanoparticles;" *Biomacromolecules* 2006, vol. 7, pp. 829-835; published on the web Feb. 15, 2006 by the Americal Chemical Society.

* cited by examiner

NANOPARTICLES FOR CYTOPLASMIC DRUG DELIVERY TO CANCER CELLS

This application claims priority to U.S. Patent Application Ser. No. 60/643,623 filed Jan. 13, 2005, and U.S. Patent Application Ser. No. 60/608,599 filed Sep. 10, 2005.

BACKGROUND OF THE INVENTION

1. Field of the Invention

The invention relates generally to nanoparticles that are used to deliver drugs into the cytoplasm of cancer cells and, more specifically, to the rapid delivery of the drugs by nanoparticles that have an inner core containing an anticancer drug and a polymer that is soluble in cancer cells.

2. Background of the Art

Cancer is the second leading cause of death in the United States. Each year more than 1.2 million Americans are diagnosed with cancer, and less than half can survive five years. Annual medical costs for cancer treatment account for billions of dollars in the US alone. Chemotherapy, which uses chemical agents (anticancer drugs) to kill cancer cells, is one of the primary methods of cancer treatment. Unfortunately, these anticancer drugs have limited selectivity for cancer and are inherently toxic to both cancer and normal tissues. As a result, anticancer drugs can cause severe side effects and damage to healthy tissues. For example cisplatin is a well-known metal complex that exhibits high antitumor activity [Rosenberg et al., 1969; Takahara et al., 1995]. However, it has significant toxicity, in particular, acute as well as chronic nephrotoxicity [von Hoff et al., 1979; Pinzani et al., 1994]. Other common side effects of anticancer drugs include decrease in the number of white blood cells (increasing risk of infection), red blood cells (losing energy) and platelets (risk for bruising and bleeding) as well as nausea, vomiting, hair loss, etc. Furthermore, the high glomerular clearance of the anticancer drugs leads to an extremely short circulation period in the blood compartment [Siddik et al., 1987].

Most importantly, treatments in conventional dosage form of these drugs may lead to initial cancer regression, but soon the cancer becomes insensitive to the drugs, causing cancer progression and death. The primary reason for the treatment failure is cancer's intrinsic and acquired drug resistance [Pastan and Gottesman, 1991; Gottesman, 2002]. When a conventional drug dose is administered intravenously, the drug molecules distribute throughout the body and some drug molecules reach the cancer interstititium. Some are taken up by cancer cells via diffusion, transport and endocytosis. On the other hand, cancer cells have various mechanisms by which they become resistant to the drugs, such as loss of a cell surface receptor or transporter for a drug to slow down the drug influx, specific metabolism of a drug, alteration by mutation or drug detoxification to consume the drugs, and the like [Gottesman, 2002]. A major mechanism of multidrug resistance is an energy-dependent drug efflux transporter, the P-glycoprotein (P-gp) pump located in cell membrane [Gottesman, 2002]. P-gp pumps are very efficient in detecting and binding a large variety of hydrophobic drugs as they enter the plasma membrane. These pumps then transport the drugs out of the cells [Bogman et al., 2001; Gottesman, 2002]. As a consequence of the slowed drug entry but efficient drug removal by the P-gp pumps and the drug consumption by other forms of drug resistance, the effective drug concentration in cytoplasm is well below the cell-killing threshold, resulting in a limited therapeutic efficacy.

Thus, a continuing challenge in cancer treatment is to develop new methodologies that have great drug selectivity for cancer and overcome the cancer drug resistance to simultaneously enhance the therapeutic efficacy and reduce toxicity to healthy tissues.

It has been demonstrated that cancer-targeted drug delivery, which preferentially delivers drugs to cancer tissues, can substantially reduce drug toxicity and enhance the therapeutic efficacy. The cancer-targeting is achieved by passive accumulation through cancer's leaky blood capillaries Hobbs et al., 1998; Monsky et al. 1999; Maeda, 2001; Jain, 2001; Torchilin, 2001]. The pore cutoff size of cancer's blood capillaries was reported ranging between 380 and 780 nm [Hobbs et al., 1998; Yuan et al., 1995] or around 400 nm [Unezaki et al., 1996]. This leaky nature allows for easier extravasation of larger molecules or colloid particles to the cancer tissues. In addition, cancer also has much fewer lymphatic capillaries than healthy tissues, such that the lymphatic drainage of macromolecules from cancer tissues is inadequate. As a result of the hyperpermeability of cancer vasculature and the absence of lymphatic drainage, macromolecules or colloidal particles are passively trapped in cancer tissues. This is referred to as the "enhanced permeability and retention effect" (EPR) [Maeda et al., 2001; Lukyanov et al., 2002]. This does not happen as much in healthy tissues because the much tighter blood vessels openings (just several nm) [Seymour, 1992] are almost impermeable for macromolecules and colloid particles. Active cancer-targeting by receptor-mediated delivery has also been achieved such as folic acid-mediated delivery [Lu et al, 2002; Gosselin and Lee, 2002]. The resulting drug concentration in the tumor can be several to tens of times higher than those in healthy tissues [Seymour, 1992; Lukyanov et al., 2002].

Of the various approaches developed for targeted drug delivery, polymer nanoparticle technique has been attracting increasing attention since it offers suitable means to deliver drugs to tissues or cells [Labhasetwar et al., 1997; Kwon, 1998; Brigger et al., 2002; Hans and Lowman, 2002]. Nanoparticles are referred to as submicron colloidal particles. Due to the subcellular size, they can penetrate through fine capillaries, cross the fenestration into interstitial space, and are easily taken up by cells via endocytosis/phagocytosis. Furthermore, nanoparticles (less than 100 nm) with a hydrophilic surface, such as a poly(ethylene glycol) (PEG) layer, can evade the recognition and subsequent uptake by the reticuloendothelial systems (RES) and thus have a prolonged circulation in the blood compartment, which is needed for the passive accumulation in cancer tissues via EPR [Gref, et al., 1994; Bogdanov et al., 1997; Moghimi et al., 2001; Kaul and Amiji, 2002]. Certain types of nanoparticles were also found to be able to overcome multidrug resistance to some extent [Brigger et al., 2002]. Nanoparticles are also much stable than liposomes and thus preclude the breakage in the bloodstream. Drugs can be physically entrapped in the core and do not experience harsh reactions. Nanoparticles also have large surfaces that can be used to modify the surface properties such as attachment of targeting ligands for site specificity.

Nanoparticles with long-circulation-times, also called stealth nanoparticles, can be fabricated from micelles formed by self-assembly of amphiphilic copolymers [Kreuter, 1994; Kwon and Kataoka, 1995; Kwon, 1998; Kataoka et al., 2001]. Such nanoparticles have a core-shell structure. The hydrophobic inner core has a high drug-loading capacity. The tight hydrophilic shell (usually composed of PEG chains) prevents the interaction of the hydrophobic core from protein adsorption and cellular adhesion and thus protects the drug in the core from hydrolysis and enzymatic degradation. The PEG chains also prevent the recognition by the RES [Moghimi et al., 2001; Brigger et al., 2002]. Thus, these so-called 'stealth' properties of the PEG shell result in an increased blood circulation time of the nanoparticles and allow drugs to passively accumulate in tumor tissues by EPR effect [Moghimi et al., 2001; Brigger et al., 2002]. These nanoparticles have been used as anticancer drug carriers such as cisplatin [Yokoyama, et al., 1996; Bogdanov et al., 1997].

The prior art has several disadvantages or drawbacks. First, the premature burst release of drugs in bloodstream is a general problem of existing nanoparticle drug carriers. A typical drug-release profile of nanoparticles suggests that the nanoparticles would immediately release drug into the bloodstream upon intravenous administration and thus only a portion of drugs reach the tumors, causing non-targeted drug release, low drug efficiency, toxicity to healthy tissues and less drug being available to cancer [Liu et al., 2001]. The initial burst release is caused by large surface area of nanoparticles and poorly entrapped drugs, or drugs adsorbed onto the outside of the particles. It has been proposed that the burst release could be minimized by creating chemical bonding of the hydrophobic polymers with the drugs, such as poly(lactic-co-glycolic acid) (PLGA) with a terminal free carboxylic acid group conjugating with DOX [Yoo et al., 2000] or covalently grafting DOX to core-forming poly(aspartic acid) [Kataoka et al., 2001]. Such nanoparticles, however, showed low or completely no anticancer activity [Yokoyama et al., 1998], because chemically bound DOX is not released due to the absence of hydrolysable link between the drug and the polymer chains of the core.

A second issue is their slow drug release. After the initial burst release, the drug release from the nanoparticles became very slow. Cancer cells have many forms of over-expressed drug resistance. If the drug influx into the cancer cell is lower than the capacity of drug removal by the P-gp pumps and the drug metabolism and detoxication etc by cancer cell's other forms of drug resistance, the drug cannot build up a concentration higher than the cell-killing threshold concentration for effective killing. The cores of existing nanoparticles are made of solid polymers and the drugs have to diffuse from the core to the outside and thus the drug release is inevitably slow.

A third issue of the nanoparticles is their slow cellular uptake by cancer cells. Because cancer cells have the P-gp pumps located in the membrane that can effectively transport the drugs out of the cell while they are in the membrane, drugs released in cell interstitium cannot effectively enter the cell plasma through the membrane. In contrast, nanoparticles in the cell release drugs directly in the tumor cell plasma and thus circumvent the P-gp pumps. Therefore, drug release inside cancer cells is preferable, but calls for efficient cellular uptake of the nanoparticles. For the PEG-coated nanoparticles, the PEG layer is used to minimize the nanoparticle interaction with RES cells to evade the clearance by RES for a long blood circulation time, but it also substantially slows down the cancer cellular uptake of the nanoparticles by the same mechanism—the steric repulsion of the PEG chains [Klibanov et al., 1990; Torchilin et al., 1992; Vittaz et al., 1996; De. Jaeghere et al., 2000]. For instance, the majority of localized PEG-coated vesicles were found not to interact with target cancer cells [Yuan et al., 1994]. As a result, PEG-coated nanoparticles may just passively accumulate in cancer interstitium and release drugs there. Receptor-mediated endocytosis by installing ligand moieties on the nanoparticle surfaces has been used to enhance the cellular uptake, e.g. transferrin receptor—transferrin [Ogris et al., 1999; Dash et al., 2000], folate receptor—folic acid [Leamon et al., 1999; Leamon and Low, 2001; Lu and Low, 2002; Kennedy et al., 2003].

Nevertheless, nanoparticles functionalized with folic acid only may not be sufficiently effective to overcome the cancer drug resistance. The steric repulsion of the nanoparticle's PEG outer layer may prevent the folic acid on the nanoparticles from finding and binding the folate receptors. Thus, the internalization of nanoparticles only via FR-mediated endocytosis (FR-Endoc) may not be fast enough to build up a cytoplasmic drug concentration exceeding the capacity of the cell's drug resistance. Hence, FR-Endoc needs to be accelerated. Furthermore, not all cancers express folate receptors. Even in FR-positive tumors, there are cells having low or no FR expression because of the cell heterogeneity. These cells cannot effectively take up the folic acid-functionalized nanoparticles and thus survive the treatment, causing relapse.

As a result of premature burst release by existing nanoparticles, slow drug release rate and low cellular uptake rate, the drug influx into the cancer cell by existing nanoparticles is still lower than the drug efflux and destruction by cell's drug resistance. The drug concentration in cancer cells is thus still lower than the cell-king threshold concentration and cannot effectively induce cell death.

Folate receptors are over-expressed on various types of cancer cells, and mediate endocytosis (FR-Endo) of folic acid-conjugated carriers. Carriers with cationic charges are easily adsorbed onto negatively charged cell membranes and enter the cell via adsorptive endocytosis (AD-Endo). In this invention, folic acid and cationic-charges dually functionalized, lysosomal pH-responsive drug releasing nanoparticles (DFNp) for fast cytoplasmic drug delivery is invented. The dual functions enable the nanoparticles to be efficiently internalized via combined endocytosis mechanisms (FR-Endo, AD-Endo, adsorption-promoted folate-receptor mediated endocytosis (AD-FR-Endo)). The nanoparticle cores are composed of polymers that are soluble at lysosomal pH (~5) and rupture the lysosomal membrane, and thereby can rapidly release drugs into the cytoplasm. Tumor targeting of the nanoparticles is achieved by passive accumulation through permeable blood capillaries, and active targeting to acidic interstitium and folate receptors. It is believed that these nanoparticles can deliver a large amount of drugs to the cytoplasm overcoming drug resistance for high therapeutic efficacy.

SUMMARY OF THE INVENTION

The invention consists of layered nanoparticles for delivering high levels of anticancer drugs to cancer cells. The nanoparticles include an outer shell, an inner core, and an intermediate layer. The core is comprised of the anticancer drug or drugs and polymer chains that are soluble at the lysosomal pH of the cancer cell. The intermediate layer is comprised of polymer chains that are insoluble at the pH of healthy tissue, but soluble at the pH of the cancer interstitium. The outer shell is comprised of water-soluble polymer chains to shield the nanoparticle from recognition by the reticuloendothelial systems so as to provide the nanoparticle with a long circulation time in the bloodstream of a subject. In an alternative embodiment, the outer shell also includes folic acid moieties that enhance the absorption of the nanoparticles by cancer cells that are over-expressing folate receptors.

A purpose of the invention is to provide a device for delivering anticancer drugs preferentially to cancer cells.

Another purpose of the invention is to provide nanoparticles for the delivery of anticancer drugs to cancer cells that have a long circulation time in the bloodstream of a subject.

A further purpose of the invention is to provide nanoparticles that are taken up quickly by cancer cells.

Yet another purpose of the invention is to provide nanoparticles with more than one active moiety on the surface to improve uptake of the nanoparticles by cancer cells of different characteristics.

Still another purpose of the invention is to provide nanoparticles for the rapid release of anticancer drugs to cancer cells that, upon entry into the cancer cell, quickly release the full load of anticancer drugs so as to raise the level of anticancer drug in the cell above the toxic level.

These and other objects of the invention will be appreciated by those skilled in the art upon a review of this specification, the associated drawings and the appended claims.

DETAILED DESCRIPTION OF PREFERRED EMBODIMENTS

Figure 1:
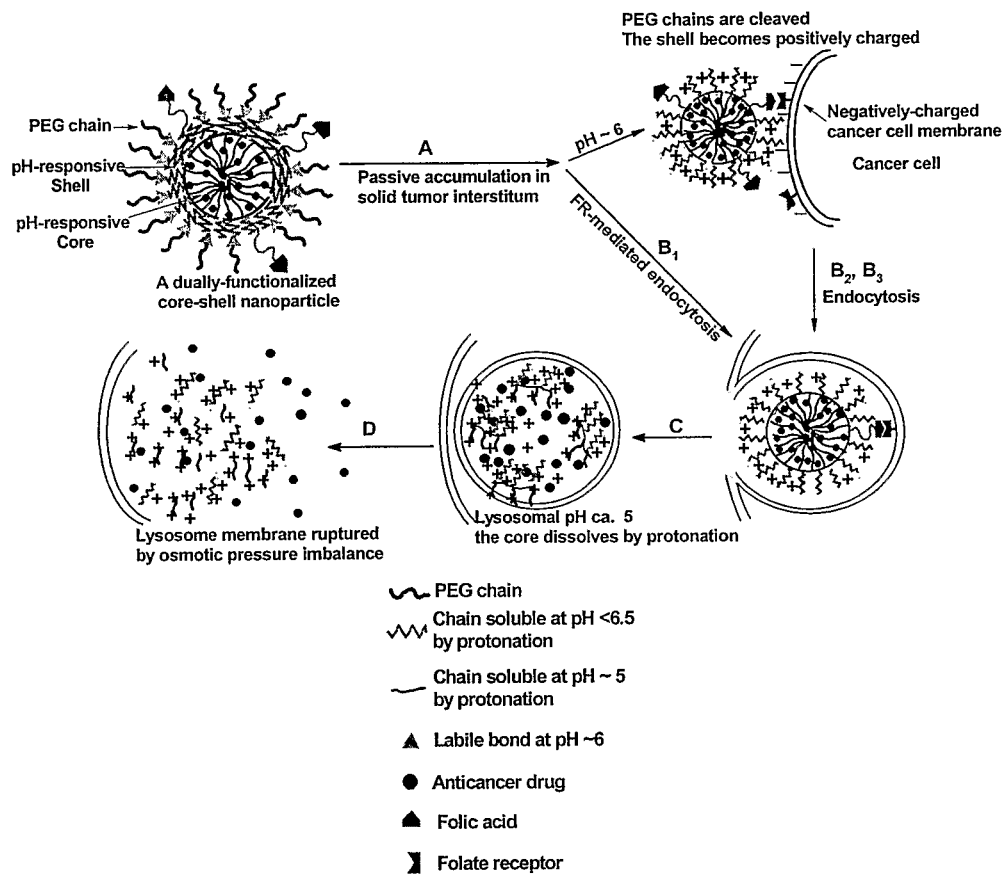
FIG. 1 is a chart of the structure and function of a dually functionalized nanoparticle of the present invention.

Nanoparticles as used in this specification include submicron colloidal particles that are able under appropriate circumstances to penetrate through capillaries, cross the fenestration into interstitial space and are taken up by cells via endocytosis/phagocytosis. Nanoparticles of the present invention are between about 10 and about 500 nm, more preferably between about 50 and about 300 nm, and most preferably between about 75 and 150 nm.

Anti-cancer drugs as used in this specification include 6-mercaptopurine, ara-CMP, bleomycin, busulfan, camptothecin sodium salt, carboplatin, carmustine, chlorambucil, chlorodeoxyadenosine, cisplatin, cyclophosphamide, cytarabine, dacarbazin, dactinomycin, daunorubicin, docetaxel, doxorubicin, etoposide, floxuridine, fludarabine phosphate, fluorouracil, gemcitabine, hexamethyl melamine, hydroxyurea, idarubicin, iphosphamide, irinotecan, lomustine, mechlorethamine, melphalan, methotrexate, mithramycin, mitomycin, mitotane, mitoxantrone, navelbine, paclitaxel, pentostatin, pipobroman, procarbazine, streptozocin, teniposide, thioguanine, thiotepa, topotecan, triethylene melamine, trimetrexate, uracil nitrogen mustard, vinblastine, vincristine, and all other anticancer drugs.

Healthy tissue pH as used in this specification means the pH of non-cancerous tissues and is most typically approximately 7.4.

Cancerous tissue interstitium pH as used in this specification means the pH of the interstitium of cancerous tissues and is in a range of between about 5.7 and 7.2 and most typically approximately 6.0.

Cancerous lysosomal pH as used in this specification means the pH inside the lysosomes of cancerous tissues and is in a range of between about 4.5 and 6.0 and most typically approximately 5.0.

Water-soluble polymer chains as used in this specification include polymer chains that are hydrophilic. Water-soluble polymer chains include polymer chains made from PEG, PEO, PDMA, and other water-soluble polymers, and copolymers thereof.

Acid labile bonds as used in this specification include chemical bonds that break at pH of approximately 7.0 or lower.

Short polymer chains as used in this specification include polymer chains that are capable of being excreted by the renal system and have a weight range of less than about 50,000 Daltons, preferentially less than 10,000.

Folate receptor over-expression as used in this specification includes the expression of one or more folate receptors by cancer cells at a rate higher than that of non-cancerous cells, and includes folate receptor expression that is increased by between about 10% and about 2000%, and more typically between about 20% and about 90%.

Nanoparticles with enhanced cellular-uptake and cancer-cell activated-instant-drug-release are prepared and administered. An outer shell is imparted on the nanoparticles using novel block-brush copolymers to inhibit premature drug release in the plasma. The long circulation time of the nanoparticle is achieved by modifying the surface with polyethylene glycol (PEG) or other hydrophilic chains that have been proven to be able to stealth the RES recognition. Electrostatic-enhanced adsorptive endocytosis is used to facilitate the cellular uptake through use of a polycation complex that is effectively taken up through the adsorptive endocytosis by the electrostatic interaction with the negatively charged cell membrane [Kabanov et al., 1998]. These positive charges are only activated and exposed at the tumor's acidic microenviroment [Helmlinger et al., 1997], but are shielded during circulation in blood stream to avoid capture by RES systems.

EXAMPLE 1

Slow- and Fast-Release Nanoparticles with a Core and a Single-Layer Corona

An example of a fast-release single-layer nanoparticles are nanoparticles with pH-responsive poly[2-(N,N-diethylamino)ethyl methacrylate) (PDEA), synthesized from PDEA-block-poly(ethylene glycol) (PDEA-PEG) copolymer using a solvent-displacement (acetone-water) method. On the other hand, nanoparticles with pH-resistant poly(ϵ-caprolactone) (PCL) cores, synthesized from PCL-block-PEG (PCL-PEG), is an example of slow-release single-layer nanoparticles. We provide the latter as a point of reference for evaluating the rate of release.

EXAMPLE 2

Cationic-Charged Functionalized Nanoparticles, for Example, Tumor-Cell-Triggered Instant-Intracellular-Drug-Releasing (IIDR) Nanoparticles The tumor-cell-triggered instant-intracellular-drug-releasing (IIDR) nanoparticles are characterized in vitro and in vivo and evaluated for enhanced cancer chemotherapy by overcoming cancer drug resistance. An example of a nanoparticle according to the present invention and its action are shown in FIG. 1.

The IIDR nanoparticle has a three-layer-onion structure with a diameter around between about 10 and 500 nm, preferably between about 50 and 300 nm and most preferably between about 75 and 150 nm. Its core-surface or shell-surface is crosslinked for improved stability. The outer layer consists of water-soluble polymer chains. These chains shield the nanoparticle from RES recognition and give the nanoparticle a long circulation time in bloodstream [Kwon, 1998; Brigger et al., 2002]. The water-soluble chains are linked to the shell with acid-labile bonds having a transition $pH_c$ of approximately 6.5 (▲). They thus peel off from the shell at the cancer interstitium, where the pH is about 6 [Helmlinger et al., 1997; Jain, 2001], to expose the shell. The shell layer consists of polymer chains insoluble at pH above approximately 6.7 but soluble at pH less than about 6.5 by being protonated to be positively charged. The shell layer thus collapses on the core and inhibits premature drug release in the bloodstream and healthy tissues, where the pH is typically approximately 7.4, but becomes positively charged in the cancer interstitium where the pH is approximately 6. The positively charged shell is easily adsorbed on the negatively charged cancer cell surface. As a result, the nanoparticle is efficiently taken up by the cell via electrostatic-interaction based adsorptive endocytosis [Kabanov et al., 1998]. The nanoparticle core is composed of anticancer drugs and polymer chains soluble at about pH 5 by being protonated to be positively charged. Accordingly, the core polymers dissolve in the lysosomes of the cancer cell, where the pH is near 5 [Reijngoud et al., 1977; Barret and Heath, 1977], to quickly release the drug payload. Furthermore, the whole structure is designed to degrade into short polymer chains for excretion out of the body after use.

Once the nanoparticles are intravenously administered, they circulate in the blood compartment. As they pass through leaky cancer capillaries, they may extravasate and be passively trapped in the cancer interstitium (A, FIG. 1). The links of the PEG chains to the shell begin to break via hydrolysis of the acid-labile bonds (▲) at the acidic cancer interstitium where the pH is approximately 6. The PEG chains are thus shed off from the nanoparticle surface to expose the shell layer. The shell layer is protonated to be positively charged at this pH. The positive charges interact with the negatively charged surface of the cancer cell and the nanoparticle is taken up via adsorptive endocytosis (B). Once the nanoparticle is transferred to a lysosome, where the pH is approximately 5, the core of the nanoparticle is also positively protonated. It thus dissolves and releases the drugs in the lysosome (C). Due to severe osmotic imbalance, the lysosome swells and its membrane is disrupted. (For amine-containing polymers as proton sponges buffering acidic lysosomes and disrupting membranes by increasing the internal osmotic pressure within the vesicle, see Boussif et al., 1995; Demeneix et al., 1996; Cherng et al., 1996; Richardson et al., 1996; Van de Wetering et al., 1999; Murthy et al., 2003). This membrane disruption quickly dumps all the carried drugs into the cytoplasm (D). The efficient cellular uptake of the nanoparticles and their instant drug release surpass the capacity of the cell's drug resistance and build up a cytoplasm drug concentration higher than the cell-killing threshold, leading to cell death. Finally, the polymers gradually degrade into short polymer chains to be excreted out of the body.

The synergetic effect of long circulation in bloodstream for effective passive accumulation in cancer tissue, the enhanced cellular uptake by electrostatic-interaction promoted endocytosis and the instant release of a large amount of different drugs to the cytoplasm to overwhelm the drug resistance render the IIDR nanoparticles a very high therapeutic efficacy for cancer with relatively minor side effects.

EXAMPLE 3

Folic Acid, Cationic-Charged Dually-Functionalized Fast-Release Nanoparticles

An alternative embodiment of the invention makes use of the folic acid moieties to enhance the uptake of the dually functionalized nanoparticles by the cancerous cells. The dually functionalized nanoparticle has a three-layer-onion structure with folic acid groups tethered on the outer layer of the nanoparticles shown in Example 2.

After intravenous administration, the nanoparticles extravasate and are trapped in the tumor interstitium (FIG. 1A). Subsequently, three endocytosis processes may occur: 1) The folic acid moieties on the nanoparticle surface may bind folate-receptors on cell membranes and trigger FR-Endo (B1); 2) In the acidic tumor interstitium, the acid-labile bonds (▲) begin to break and the PEG chains are shed off from the nanoparticle surface to expose the shell layer, the shell layer is positively charged at this pH and thus adsorbed on the negatively-charged cell membrane, leading to electrostatically adsorptive endocytosis (AD-Endo) (B2); and 3) the adsorption of the nanoparticle on the cell surface also makes it easy for folic acid find and bind folic receptors on the cell surface, resulting in adsorption-promoted FR-mediated endocytosis (AD-FR-Endo) (B3). Once the nanoparticle is transferred to a lysosome, where the pH is about 5, the core of the nanoparticle is also positively protonated. It dissolves and releases all the drugs in the lysosome (C). Due to severe osmotic imbalance caused by the amine-containing polymers, the lysosome swells, rupturing its membrane. This membrane disruption instantly dumps all the carried drugs into the cytoplasm (D). The polymers gradually degrade into short polymer chains to be excreted out of the body.

The combined receptor and electrostatic adsorption-mediated endocytosis will further enhance the cellular uptake of the nanoparticles and, and the combined mechanisms of endocytosis also make the nanoparticles effective for various types of cancer cells to prevent cancer relapse.

Results

1. Synthesis of Polymers with Different Transition pHs

Figure 2:
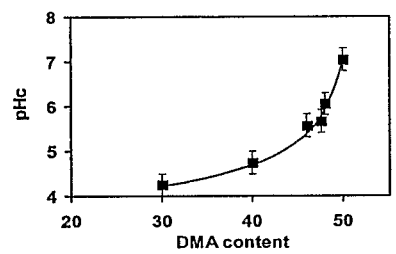
FIG. 2 is a chart of a DMA/DEA random copolymer with different compositions and their corresponding transition pH ($pH_c$).

Polymers having a transition pH (pHc) near 5 and 6.5 (pHc is the pH above which the polymer is insoluble) are synthesized for the pH-responsive nanoparticles. Poly[2-(N,N-dimethylamino)ethyl methacrylate] (PDMA) is soluble at all pH ranges, while the pHc of poly[2-(N,N-diethylamino)ethyl methacrylate] (PDEA) is about 3 to 4. The random copolymers of 2-(N,N-diethylamino)ethyl methacrylate (DEA) and 2-(N,N-dimethylamino)ethyl methacrylate (DMA) have pHc depending on their compositions, as shown in FIG. 2. For example, poly(DMA48%-co-DEA52%) has a pHc at 6.5.

2. Synthesis of PEG-Block-PDEA Copolymers with Controlled Chain Lengths

CuBr/HMTETA effectively polymerized DEA with good control in PDEA Mn, regardless of the PEG chain length of the macroinitiator (PEG45-Br, PEG113-Br). Well-defined block copolymers with controlled block lengths are synthesized.

3. Synthesis of Hydrolysable Link for PEG Chains

Figure 3:
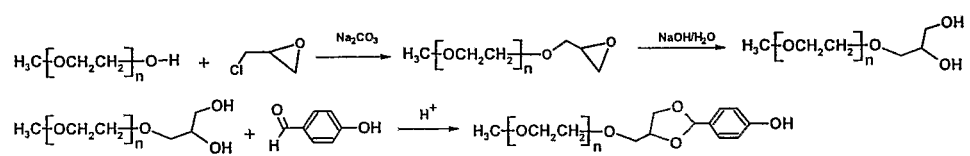
FIG. 3 is a diagram of the synthesis of PEG-acetal of hydroxybenzaldehyde.

An example of the PEG link that is labile at pH ~6 but stable at pH 7.4 is synthesized by tethering PEG chain on the acetal of p-hydroxybenzaldehyde, which have pH-dependent hydrolysis rate [Fife et al., 1996]. The PEG chain was functionalized with a diol moiety, which reacted with the hydroxybenzaldehyde to produce the acetal group (FIG. 3). The phenol group is used to link with other chains. Optimization of the reaction conditions of each step led to the final product (a) with 97% purity.

Figure 4:
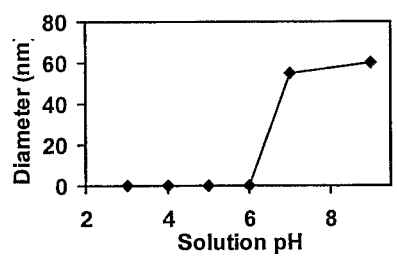
FIG. 4 is a chart of nanoparticle size as a function of pH.

4. Synthesis of Nanoparticles by pH-Controlled Fabrication and their pH-Dependent Solubility The nanoparticles of PEG-block-PDEA were synthesized by pH-controlled micelle formation. The block polymer was dissolved as a clear solution at pH2. When the solution pH was increased to 8, the solution became slightly milky. If the solution pH was decreased back to 2, the solution became clear again. The particle size measured by dynamic light scattering was found to be pH dependent. For example, at a pH above 7, PEG45-PDEA100 formed approximately 60 nm nanoparticles. At pH<6, there was no particle detected (FIG. 4). The length of each block strongly affects the sizes of the nanoparticles (Table 1).

TABLE 1

Sizes of PEG-block-PDEA Nanoparticles

| PEG | DEA | Dp(nm) |
|---|---|---|
| 5000 | 8500 | 20 |
| 5000 | 12000 | 30 |
| 2000 | 12000 | 37 |
| 2000 | 16000 | 64 |

FIG. 4 also indicates that the nanoparticles have pH-dependent solubility: At pH<6, the nanoparticles dissolve. By optimizing the composition, the nanoparticles are made soluble at pH ~5 for fast release.

Figure 5:
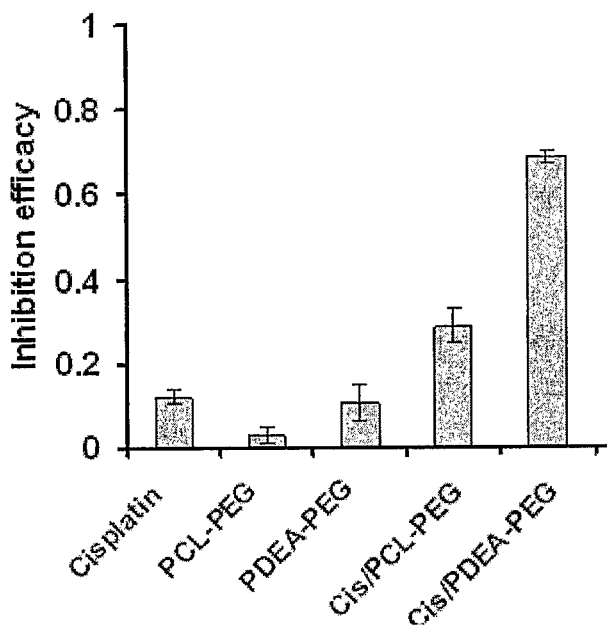
FIG. 5. is a chart of the cytotoxicity of free and nanoparticle-encapsulated cisplatin to SKOV-3 adenocarcinoma cancer cells (2 h treatment) estimated with MTT Cell Proliferation Assay; cisplatin dose, 0.25 µg/mL; data represent mean value±S.E.

5. In Vitro Characterization—Cytostatic Effects of Cisplatin/Nanoparticles on Epithelial Ovarian Cancer Cells SKOV-3 cells were obtained from American Type Culture Collection (ATCC; Rockville, Md., USA) and propagated to confluence in T-75 flasks (Corning Costar, Cambridge, Mass., USA) at 37° C. in a humidified atmosphere of 95% air and 5% $CO_2$ in 15 ml of RPMI-1640 media supplemented with 10% fetal bovine serum, 10 µg/ml insulin, and antibiotic/antimycotic solution (A9909). Cells were harvested from exponential phase cultures with 0.25% trypsin/0.03% EDTA, transferred into culture plates ($7.5 \times 10^4$ cells/ml; 200 µl/well), and incubated for 47 h. Treatments were added in fresh replacement media (100 µl of cisplatin/nanoparticles solution, n=3; cisplatin=0.25 µg/ml) for 2 h, and the cell inhibition was estimated using MTT assay. FIG. 5 shows that cisplatin in the fast-releasing nanoparticles made of PDEA-PEG has a significantly higher cytotoxicity than free and slow-release PCL-PEG nanoparticle-encapsulated cisplatin.

6. In Vivo Characterization—Antitumor Effects of Cisplatin/Nanoparticles in Immunocompromised Mice At four weeks post-inoculation mice were treated ip with 0.1 ml PBS (vehicle control), PDEA-PEG (blank nanoparticle control), cisplatin, or cisplatin/PDEA-PEG. Four mice were included in each group. Equivalent doses of 10 mg/kg cisplatin were administered. Mice were killed (cervical dislocation) at 6 h post-treatment. Intestines/mesentery were excised and fixed by immersion in Histochoice (Amersco, Solon, Ohio, USA). Tumor samples were washed in PBS, dehydrated, cleared, infiltrated with paraffin wax, and cross-sectioned at a thickness of 7 µm. Sections were floated onto microscope slides, air-dried, deparaffinized in xylene, rehydrated, stained in hematoxylin and eosin, and examined by light microscopy. One field from each of three tumors per mouse was subjected to morphometric analyses. Numbers of pyknotic (apoptotic) and healthy cells were counted at ×1000 magnification. Vascular spaces were ascertained at ×200 with the aid of Optimas Image Analysis Software (Bothell, Wash., USA).

Figure 6:
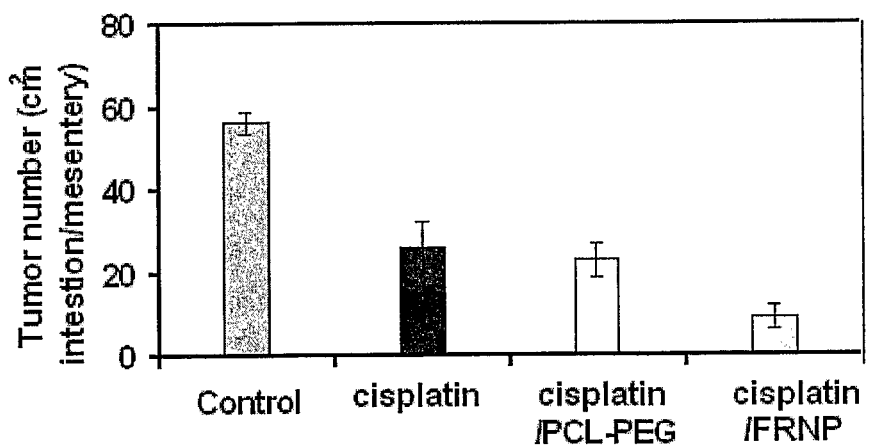
FIG. 6 is a chart of the tumor number per $cm^3$ of the intestine and mesentery of mice inoculated with ovarian cancer cells and following treatment with a control, free cisplatin, cisplatin in normal polycaprolacton-based nanoparticles, and cisplatin in fast releasing (FRNP) PDEA/PEG nanoparticles of the present invention.
Figure 7:
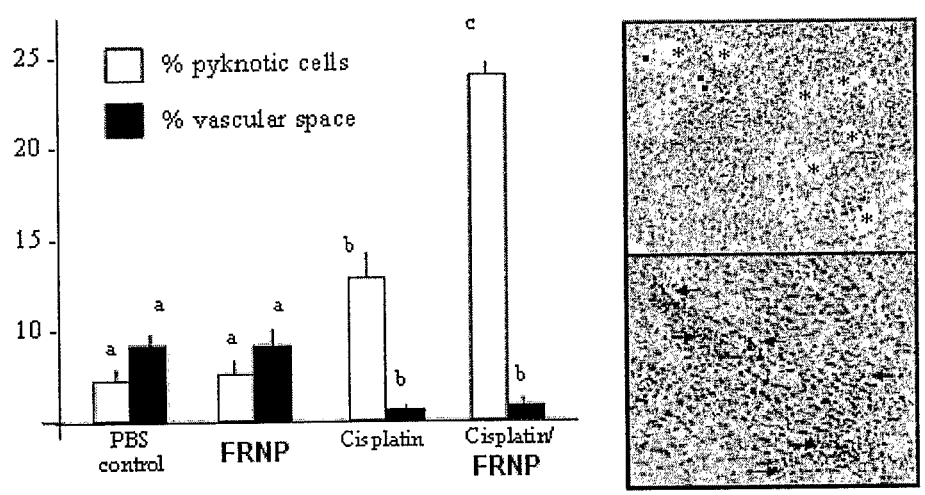
FIG. 7 is a chart of the morphometric analyses of tumor tissue sections taken from the four groups of mice as in FIG. 6 and two micrographs comparing the free cisplatin group with the cisplatin in FRNP PDEA/PEG nanoparticle group.

Additional groups of mice were treated with PBS, cisplatin, cisplatin/PDEA-PEG, or cisplatin/PCL-PEG (n=4) at 4 and 5 weeks post-inoculation and killed at 6 weeks. Tumor nodules were counted along a 1 $cm^2$ segment of intestine/mesentery at each of three different sites. The Group 4 mice exhibited a significant (p<0.05) decrease in the number of tumors present over the Group 2 mice (FIG. 6). Histological sections of the intestine/mesentery were taken 6 hours after the second treatment and examined microscopically. Morphometric analyses of the sections showed a marked increase in the of pyknotic (dying) cells and decrease in vascular space in the tumor of the Group 4 mice (FIG. 7).

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

References

Barret, A. and Heath, M. In Lysosomes: A Laboratory Handbook, $2^{nd}$ ed.; Dingle, J., Ed.; North-Holland: New York, 1977.

Bogdanov, A., Jr.; Wright, S.C.; Marecos, E. M.; Bogdanova, A.; Martin, C.; Petherick, P.; Weissleder, R. A long-circulating copolymer in "passive targeting" to solid tumors, *J. Drug Targeting* 4 (1997), 321-330.

Bogman, K.; Peyer, A. K.; Torok, M.; Kusters, E.; Drewe, J. HMG-CoA reductase inhibitors and P-glycoprotein modulation, *Br. J. Pharmacol.* 132 (2001), 1183-92.

Boussif, O.; Lezoualc'h, F.; Zanta, M. A.; Mergny, M. D.; Scherman, D.; Demeneix, B.; Behr, J-P. A versatile vector for gene and oligonucleotide transfer into cells in culture and in vivo: polyethylenimine. PNAS (1995), 92(16), 7297-301.

Brigger, I.; Dubernet, C.; Couvreur, P. Nanoparticles in cancer therapy and diagnosis, *Adv. Drug Delivery. Rev.* 54 (2002), 631-651.

Cherng, J. Y.; Van de Wetering, P.; Talsma, H.; Crommelin, D. J. A.; and Hennink, W. E. Effect of size and serum proteins on transfection efficiency of poly(2-(dimethylamino)-ethyl methacrylate)-plasmid nanoparticles, *Pharmacol. Res.* 13 (1996), 1038-1042.

Dash, P. R.; Read, M. L.; Fisher, K. D.; Howard, K. A.; Wolfert, M.; Oupicky, D.; Subr, V.; Strohalm, J.; Ulbrich, K.; Seymour, L. W. Decreased binding to proteins and cells of polymeric gene delivery vectors surface modified with a multivalent hydrophilic polymer and retargeting through attachment of transferrin, *J. Biol. Chem.* 275 (2000), 3793-3802.

De. Jaeghere, F.; Allemann, E.; Feijen, J.; Kissel, T.; Doelker, E.; Gurny, R. Cellular uptake of PEO surface-modified nanoparticles: evaluation of nanoparticles made of PLA: PEO diblock and triblock copolymers, *J. Drug Targeting*, 8 (2000), 143-153.

Demeneix, B. A. and Behr J.-P. In *Artificial Self-Assembling Systems for Gene Delivery Eds.:* Felgner, P. L.; Heller, M. J.; Lehn, P.; Behr, J. P.; Szoka, Jr., F. C. ACS, Washington, D.C., (1996), 146-151.

T. H.; Bembi, R. and Natarajan R. Neighboring carboxyl group participation in the hydrolysis of acetals. Hydrolysis of o-carboxybenzaldehyde cis- and trans-1,2-cyclohexanediyl acetals, *J. Am. Chem. Soc.* 118 (1996), 12956-12963.

Gosselin, M. A. and Lee, R. J. Folate receptor-targeted liposomes as vectors for therapeutic agents, *Biotechnol. Annu. Rev.* 8 (2002), 103-131.

Gottesman, M. M. Mechanisms of cancer drug resistance, *Annu. Rev. Med.* 53 (2002), 615-627.

Gref, R.; Minamitake, Y.; Peracchia, M. T.; Trubetskoy, V.; Torchilin, V.; Langer, R. Biodegradable long-circulating polymeric nanospheres, *Science* 263 (1994), 1600-1603.

Hans, M. L. and Lowman, A. M. Biodegradable nanoparticles for drug delivery and targeting, *Current Opini. Solid State Mater. Sci.* 6 (2002), 319-327.

Helmlinger, G.; Yuan, F.; Dellian, M.; Jain, R. K. Interstitial pH and $PO_2$ gradients in solid tumors in vivo: simultaneous high-resolution measurements reveal a lack of correlation, *Nat. Med.* 3 (1997), 177-182.

Hobbs, S. K.; Monsky, W. L.; Yuan, F.; Roberts, W. G.; Griffith, L.; Torchilin, V. P.; Jain, R. K. Regulation of transport pathways in tumor vessels: role of tumor type and microenvironment, *Proc. Natl. Acad. Sci. USA* 95 (1998), 4607-4612.

Jain, R. K. Delivery of molecular medicine to solid tumors: lessons from in vivo imaging of gene expression and function, *J. Control. Release* 74 (2001), 7-25.

Kabanov, A. V.; Felgner, P. L.; Seymour, L. W. (Eds.), Self-assembling Complexes for Gene Delivery, John Wiley, Chichester, UK, 1998.

Kataoka, K.; Harada, A.; Nagasaki, Y. Block copolymer micelles for drug delivery: design, characterization and biological significance, *Adv. Drug Delivery Rev.* 47 (2001), 113-131.

Kaul, G. and Amiji, M. Long-circulating poly(ethylene glycol)-modified gelatin nanoparticles for intracellular delivery, *Pharm. Res.* 19 (2002), 1061-1067.

Kennedy, M. D.; Jallad, K. N.; Lu, J.; Low, P. S.; Ben-Amotz, D. Evaluation of folate conjugate uptake and transport by the choroid plexus of mice, *Pharma. Res.* 20 (2003), 714-719.

Klibanov, A. L.; Maruyama, K.; Torchilin, V. P. and Huang. L. Amphipathic polyethyleneglycols effectively prolong the circulation time of liposomes, *FEBS Lett.* 268 (1990), 235-237.

Kreuter, J. *Nanoparticles*, in: J. Kreuter (Ed.), Colloidal Drug Delivery Systems, Marcel Dekker, New York, (1994), 219-342.

Kwon, G. S, and Kataoka, K. Block copolymer micelles as long-circulating drug vehicles, *Adv. Drug Delivery Rev.* 16 (1995), 295-309.

Kwon, G. S. Diblock copolymer nanoparticles for drug delivery, *Crit. Rev. Ther. Drug Carrier Syst.* 15 (1998), 481-512.

Labhasetwar, V.; Song, C.; Levy, R. J. Nanoparticle drug delivery system for restenosis, *Adv. Drug Delivery Rev.* 24 (1997), 63-85.

Leamon, C. P.; Weigl, D.; Hendren, R. W. Folate copolymer-mediated transfection of cultured cells, *Bioconjug. Chem.* 10 (1999), 947-957.

Leamon, C. P. and Low, P. S. Folate-mediated targeting: from diagnostics to drug and gene delivery, *Drug Discovery Today* 6 (2001), 44-51.

Liu, L.; Li, C.; Li, X.; Yuan, Z.; An, Y.; He, B. Biodegradable polylactide/poly(ethylene glycol)/polylactide triblock copolymer micelles as anticancer drug carriers, *J. Appl. Polym. Sci.,* 80 (2001), 1976-1982.

Lu, Y. and Low, P. S. Folate-mediated delivery of macromolecular anticancer therapeutic agents, *Adv. Drug Delivery Rev.* 54 (2002), 675-693.

Lu, Y. and Low, P. S. Immunotherapy of folate receptor-expressing tumors: review of recent advances and future prospects, *J. Control. Release* 91 (2003), 17-29.

Lukyanov, A. N.; Gao, Z.; Mazzola, L.; Torchilin, V. P. Polyethylene glycol-diacyllipid micelles demonstrate increased accumulation in subcutaneous tumors in mice, *Pharm. Res.* 19 (2002), 1424-1429.

Maeda, H. The enhanced permeability and retention (EPR) effect in tumor vasculature: the key role of tumor-selective macromolecular drug targeting, *Adv. Enzyme Regul.* 41 (2001), 189-207.

Moghimi, S. M.; Hunter, A. C. and Murray, J. C. Long-circulating and target-specific nanoparticles: theory to practice, *Pharmacol. Rev.* 53 (2001), 283-318.

Monsky, W. L.; Fukumura, D.; Gohongi, T.; Ancukiewcz, M.; Weich, H. A.; Torchilin, V. P.; Jain, R. K. Augmentation of transvascular transport of macromolecules and nanoparticles in tumors using vascular endothelial growth factor, *Cancer Res.* 59 (1999), 4129-4135.

Murthy, N.; Campbell, J.; Fausto, N.; Hoffman, A. S.; Stayton, P. S. Design and synthesis of pH-responsive polymeric carriers that target uptake and enhance the intracellular delivery of oligonucleotides, *J. Control. Release* 89 (2003), 365-374.

Ogris, M.; Brunner, S.; Schuller, S.; Kircheis, R.; Wagner, E. PEGylated DNA/transferrin-PEI complexes: reduced interaction with blood components, extended circulation in blood and potential for systemic gene delivery, *Gene Ther.* 6 (1999), 595-605.

Pastan, I. and Gottesman, M. M. Multidrug resistance, *Annu. Rev. Med.* 42 (1991), 277-286.

Pinzani, V.; Bressolle, F.; Hang, L. J.; Galtier, M.; Blayac, J. P.; Balmes, P. Cisplatin-induced renal toxicity and toxicity-modulating strategies—a review, *Cancer Chemother. Pharmacol.* 35 (1994), 1-9.

Reijngoud, D. J. and Tager, J. M. The permeability properties of the lysosomal membrane, *Biochim. Biophys. Acta* 472 (1977), 419-449.

Richardson, S.; Ferruti, S.; Duncan, R. Poly(amidoamine)s as potential endosomolytic polymers: evaluation in vitro and body distribution in normal and tumor bearing animals, *J. Drug Target.* 6 (1996), 391-397.

Rosenberg, B.; VanCamp, L.; Trosko, J. E.; Mansour, V. H. Platinum compounds: a new class of potent antitumor agents, *Nature* 222 (1969), 385.

Scholes, P. D.; Coombes, A. G. A.; Davis, M. C.; Ilium, L.; Davis, S. S. Particle engineering of biodegradable colloids for site-specific drug delivery, in: K. Park (Ed.), Controlled Drug Delivery. Challenges and Strategies, ACS, Washington, D.C., (1997), 73-106.

Seymour, L. W. Passive tumor targeting of soluble macromolecules and drug conjugates, *Crit. Rev. Ther. Drug Carrier Syst.* 9 (1992), 135-187.

Siddik, Z. H.; Newell, D. R.; Boxall, F. E.; Harrap, K. R. The comparative pharmacokinetics of carboplatin and cisplatin in mice and rats, *Biochem. Pharmacol.* 36 (1987), 1925-1932.

Takahara, P. M.; Rosenzweig, A. C.; Frederick, C. A.; Lippard, S. J. Crystal-structure of double-stranded DNA containing the major adduct of the anticancer drug cisplatin, *Nature* 377 (1995), 649-652.

Torchilin, V. P.; Klibanov, A. L.; Huang, L.; O'Donnell, S. M.; Nossiff, N. and Khaw. B. A. Targeting accumulation of polyethylene glycol-coated (immuno)liposomes in infarcted rabbit myocardium, *FASEB J.* 6 (1992), 2716-2719.

Torchilin, V. P. Structure and design of polymeric surfactant-based drug delivery systems, *J. Control. Release* 73 (2001), 137-172.

Unezaki, S.; Maruyama, K.; Hosoda, J.-I.; Nagae, I.; Koyanagi, Y.; Nakata, M.; Ishida, O.; Iwatsuru, M.; Tsuchiya, S. Direct measurement of the extravasation of polyethyleneglycol-coated liposomes into solid tumor tissue by in vivo fluorescence microscopy, *Int. J. Pharm.* 144 (1996) 11-17.

Van de Wetering, P.; Moret, E. E.; Schuurmans-Nieuwenbroek, N. M. E.; van Steenbergen, M. J.; and Hennink, W. E. Structure-activity relationships of water-soluble cationic methacrylate/methacrylamide polymers for nonviral gene delivery, Bioconjug. Chem. 10 (1999), 589-597.

Vittaz, M.; Bazile, D.; Spenlehauer, G.; Verrecchia, T.; Veillard, M.; Puisieux, F.; Labarre, D. Effect of PEO surface density on long-circulating PLA-PEO nanoparticles which are very low complement activators, *Biomaterials* 17 (1996), 1575-1581.

Von Hoff, D. D.; Schilsky, R.; Reichert, C. M.; Reddick, R. L.; Rozencweig, M.; Young, R. C.; Muggia, F. M. Toxic effects of cis-dichlorodiammineplatinum(II) in man, *Cancer Treat. Reports* 63 (1979), 1527-1531.

Yokoyama, M.; Okano, T.; Sakurai, Y.; Suwa, S.; Kataoka, K. Introduction of cisplatin into polymeric micelles, *J. Control. Release* 39 (1996), 351-356.

Yokoyama, M.; Fukushima, S.; Uehara, R.; Okamoto, K.; Kataoka, K.; Sakurai, Y.; Okano, T. Characterization of physical entrapment and chemical conjugation of adriamycin in polymeric micelles and their design for in vivo delivery to a solid tumor, *J. Control. Release* 50 (1998), 79-92.

Yoo, H. S.; Lee, K. H.; Oh, J. E.; Park, T. G. In vitro and in vivo anti-tumor activities of nanoparticles based on doxorubicin—PLGA conjugates, *J. Control. Release* 68 (2000) 419-431.

Yuan, F.; Dellian, M.; Fukumura, D.; Leuning, M.; Berk, D. D.; Yorchilin, V. P.; Jain, R. K. Vascular permeability in a human tumor xenograft: molecular size dependence and cutoff size, *Cancer Res.* 55 (1995), 3752-3756.

Yuan, F.; Dellian, M.; Fukumura, D.; Leuning, M.; Berk, D. D.; Yorchilin, V. P.; Jain, R. K. Vascular permeability in a human tumor xenograft: molecular size dependence and cutoff size, *Cancer Res.* 55 (1995), 3752-3756.

We claim:

1. A layered nanoparticle that, when administered to a subject, releases an anticancer drug within a cancer cell, the layered nanoparticle comprising:
   a block copolymer micelle, comprising poly[2-(N,N-dimethylamino)ethyl methacrylate](PDMA) and poly[2-(N,N-diethylamino)ethyl methacrylate](PDEA);
   (a) an outer layer of water-soluble polymer chain moieties;
   (b) an inner core layer containing the anticancer drug and polymer chains that dissolve in the cancer cell; and
   (c) an intermediate layer between the outer layer and the inner core layer, the intermediate layer being insoluble at a pH of about 7.4 but soluble at the pH of a cancer interstitium, wherein the pH of said cancer interstitium is between 5.6 and 6.4.

2. A layered nanoparticle as defined in claim 1, further comprising folate moieties in the outer layer.

3. A layered nanoparticle as defined in claim 1, wherein the water-soluble polymer chain moieties are selected from the group consisting of PEG, PEO, PDMA, PVA (polyvinyl alcohol) and co-polymers of thereof.

4. A layered nanoparticle as defined in claim 1, wherein the anticancer drug is selected from the group consisting of 6-mercaptopurine, ara-CMP, bleomycin, busulfan, camptothecin sodium salt, carboplatin, carmustine, chlorambucil, chlorodeoxyadenosine, cisplatin, cyclophosphamide, cytarabine, dacarbazin, dactinomycin, daunorubicin, docetaxel, doxorubicin, etoposide, floxuridine, fludarabine phosphate, fluorouracil, gemcitabine, hexamethyl melamine, hydroxyurea, idarubicin, iphosphamide, irinotecan, lomustine, mechlorethamine, melphalan, methotrexate, mithramycin, mitomycin, mitotane, mitoxantrone, navelbine, paclitaxel, pentostatin, pipobroman, procarbazine, streptozocin, teniposide, thioguanine, thiotepa, topotecan, triethylene melamine, trimetrexate, uracil nitrogen mustard, vinblastine, and vincristine.

5. A layered nanoparticle as defined in claim 1, wherein the size of the nanoparticle is limited to the range of between 10 and 500 nm.

6. A layered nanoparticle as defined in claim 1, wherein the outer layer is insoluble in healthy tissue above a pH of about 6.7.

7. A layered nanoparticle as defined in claim 1, wherein the inner core is soluble in the cancer cell, below a pH of 5.3.

* * * * *